United States Patent [19]

Grenier

[11] Patent Number: 5,239,568
[45] Date of Patent: Aug. 24, 1993

[54] RADIATION COLLIMATOR SYSTEM

[75] Inventor: Raymond P. Grenier, Milwaukee, Wis.

[73] Assignee: Scinticor Incorporated, Milwaukee, Wis.

[21] Appl. No.: 605,721

[22] Filed: Oct. 29, 1990

[51] Int. Cl.⁵ ............................................. G21K 1/02
[52] U.S. Cl. ................................... 378/147; 378/145; 378/51; 378/154; 250/505.1; 250/518.1
[58] Field of Search ............... 378/147, 417, 148, 145, 378/149, 152, 154, 51; 250/505.1, 310, 306, 518.1

[56] References Cited

U.S. PATENT DOCUMENTS

| | | | |
|---|---|---|---|
| 3,257,560 | 6/1966 | Jones | 378/147 |
| 3,781,564 | 12/1973 | Lundberg | 250/505.1 |
| 4,096,389 | 6/1978 | Ashe et al. | 250/505.1 |
| 4,194,123 | 3/1980 | Wittry | 378/147 |
| 4,465,540 | 8/1984 | Albert | 250/503.1 |
| 4,582,999 | 4/1986 | Dance et al. | 250/505.1 |
| 4,825,454 | 4/1989 | Annis et al. | 378/147 |
| 4,951,305 | 8/1990 | Moore et al. | 378/145 |
| 5,099,134 | 3/1992 | Hase et al. | 378/154 |

Primary Examiner—David P. Porta
Assistant Examiner—Kim-Kwok Chu
Attorney, Agent, or Firm—Reinhart, Boerner, Van Deuren, Norris & Rieselbach

[57] ABSTRACT

A collimator assembly for removing selected radiation output from a specimen. The assembly includes collimator elements with each element having walls comprised of a first material covered by an inner layer of a second material which preferentially absorbs inelastic scattered radiation created in the first material.

13 Claims, 13 Drawing Sheets

| B<br>SVC<br>0.75 | RA<br><br>1.5 | RA<br>RAV<br>2.25 | RA<br>RV<br>PA 3.0 | RH<br>RL<br>3.75 | PA<br>RL<br>LL 4.5 | PA<br>L<br>5.25 |
|---|---|---|---|---|---|---|
| PA<br>L<br>6.0 | L<br><br>6.75 | L<br><br>7.5 | L<br>LA<br>8.25 | L<br>LA<br>LV 9.0 | L<br>LA<br>LV 9.75 | LA<br>LV<br>AO 10.5 |
| LV<br>AO<br>AT 11.25 | LV<br>AO<br>AT 12.0 | LV<br>AO<br>AT 12.75 | LV<br>AO<br>DA 13.5 | LH<br><br>14.25 | LH<br><br>15.0 | LH<br><br>15.75 |
| LH<br><br>16.5 | LH<br><br>17.25 | LH<br><br>18.0 | LH<br>MY<br>18.75 | LH<br>MY<br>19.5 | LH<br>RH<br>20.25 | LH<br>RH<br>21.0 |
| RC<br><br>21.75 | RC<br><br>22.5 | RC<br><br>23.25 | RC<br><br>24.0 | RC<br><br>24.75 | RC<br><br>25.5 | RC<br><br>26.25 |

RADIATION COLLIMATOR SYSTEM

BACKGROUND OF THE INVENTION

This invention is generally concerned with a collimator for removing unwanted divergent beams of radiation received from a source, leaving a well resolved radiation beam for detection and analysis. More particularly, the invention is directed to a collimator having a layered structure for removing not only unwanted angularly divergent radiation beams, but also for removing radiation inelastically scattered by the collimator structure itself.

Radiographic imaging methods and apparatus are undergoing rapid evolution as efforts are being made to improve the ability to image selected portions of a specimen or diffract and sense radiation from the specimen. The effectiveness of these various methodologies and even the ability to use certain techniques depends primarily on spatial resolution and on the associated signal to noise ratio in the data being accumulated. Present technology is able to generate a radiation intensity adequate to image and evaluate structure and analyze a number of abnormalities. However, current technology cannot effectively collimate this radiation intensity without counting certain divergent radiation and thus including substantial unwanted noise in the resulting data. Such divergent, unwanted signal derives, for example, from radiation which has been inelastically scattered from the collimator structure itself. This deficiency therefore requires exposing the specimen to larger intensities of radiation in order to achieve a desired resolution. Unfortunately, such increased radiation exposure can be hazardous, and moreover there are some divergent radiation sources whose deleterious effects cannot be alleviated even by increasing the radiation signal level.

It is therefore an object of the invention to provide an improved method of manufacture and method for collimation of radiation.

It is another object of the invention to provide a new method of manufacture of a collimator for a radiation beam.

It is a further object of the invention to provide an improved collimating device for removing divergent radiation beams received from, or passed through, a specimen undergoing diagnostic analysis.

It is an additional object of the invention to provide a new radiation collimator assembly for providing highly resolved, high intensity data characteristic of a specimen but without having to increase exposure to radiation.

It is yet another object of the invention to provide an improved radiation collimator assembly having a layered wall material structure for substantially reducing inelastic scattered radiation present in the detected data signal.

It is still a further object of the invention to provide a new collimator having a lead base structure with an outer layer of a material which preferentially absorbs X-rays generated from inelastic scattering of gamma rays from the lead base collimator structure.

It is yet an additional object of the invention to provide a radiation collimator having a selectable collimator length using a stack of different predetermined height collimator units.

It is still a further object of the invention to provide a gamma ray collimator of lead with a thin tin layer on the collimator walls to absorb lead X-rays generated by inelastic gamma ray scattering from the lead collimator.

Other objects, features and advantages of the present invention will be readily apparent from the following description of the preferred embodiments thereof, taken in conjunction with the accompanying drawings described below wherein like elements have like numerals throughout the several views.

DETAILED DESCRIPTION OF PREFERRED EMBODIMENTS

Figure 1:
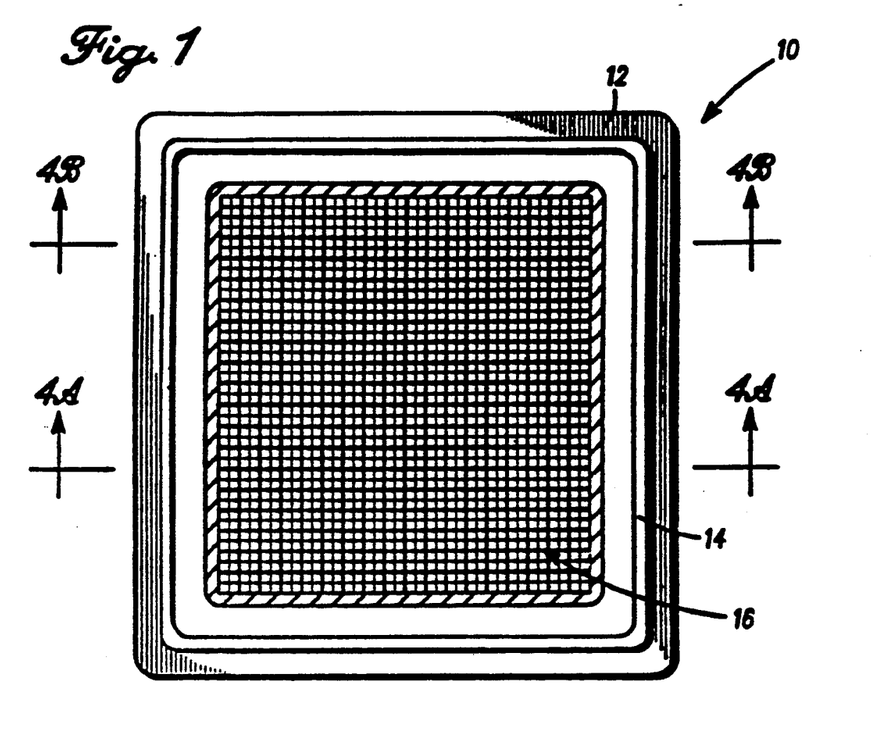
FIG. 1 shows an incident radiation view of a collimator assembly.

A gamma ray collimator assembly constructed in accordance with the invention is shown generally at 10 in FIG. 1. The collimator assembly 10 includes a housing 12, typically constructed of aluminum. Coupled to the housing 12 is a side shielding 14 which is normally constructed of lead when the collimator assembly 10 is used for collimation of gamma rays. Disposed within the housing 12 and coupled to the side shielding 14 are collimator elements 16 constructed of collimator walls 18 (best seen in FIGS. 2–4).

Figure 2:
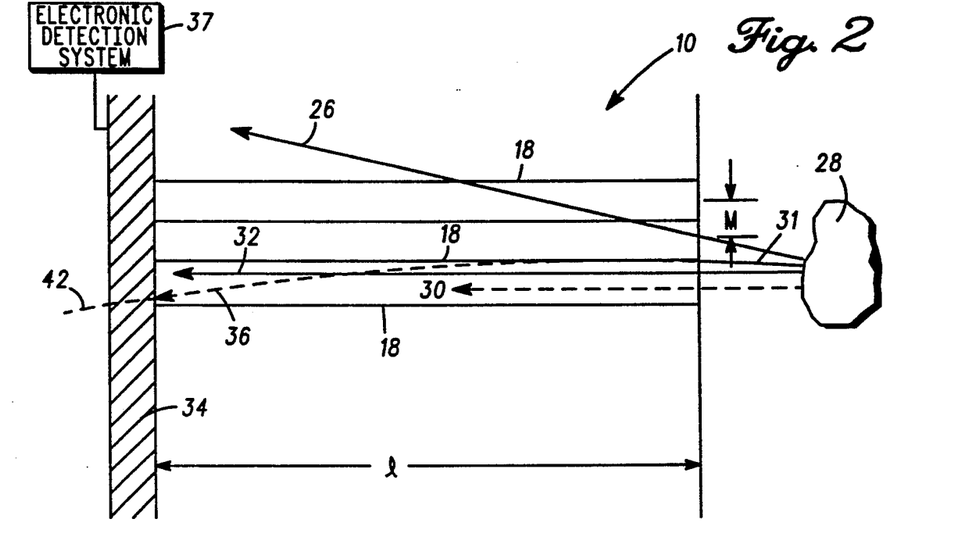
FIG. 2 shows a side view of a cross section of a single vertical stack of collimators.
Figure 3:
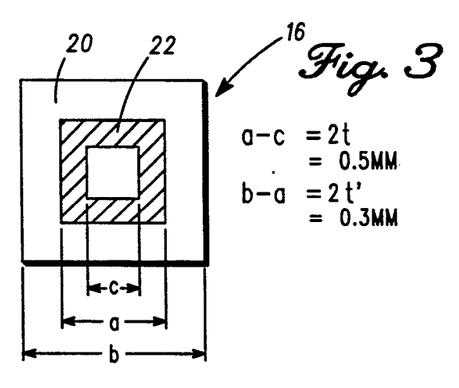
FIG. 3 illustrates a top, or face, view of one embodiment of a collimator.
Figure 4A:
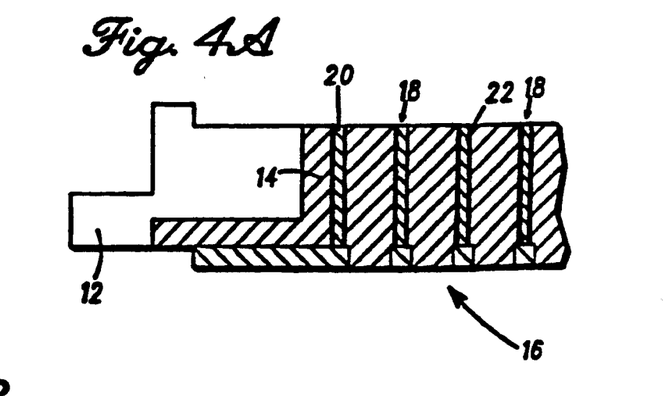
FIG. 4A shows a cross section taken along line 4A—4A in FIG. 1
Figure 4B:
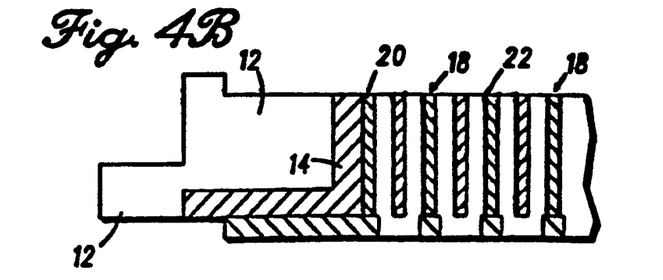
FIG. 4B shows a cross section taken along line 4B—4B in FIG. 1.

In a preferred embodiment the collimator walls 18 are constructed of a layered material with a base material structure 20 and a thin layer 22 disposed thereon (see FIGS. 2 and 3). The radiation used in a conventional radiographic embodiment is high energy X-rays or gamma rays, and in a preferred embodiment the base material structure 20 is lead and the thin layer 22 is tin. For example, as shown in FIG. 3 in a preferred geometry the collimator walls 18 are square cross section tubing with lead being the base material structure 20 (hereinafter "lead structure 20") and tin being the thin layer 22. The tin can be readily coupled to the lead structure 20 by conventional methods such as electroplating, evaporation, ion deposition and mechanical lamination.

Operation of the collimator assembly 10 is best illustrated in FIG. 2. In this example, the radiation is gamma radiation, and gamma rays 26 originate from a conventional radionuclide source, such as cobalt, thallium or technitium, which is passed through a specimen 28 (depicted schematically). As the radioactive radionuclide source decays it emits characteristic gamma rays which are emitted from or pass through the specimen 28 and form an image, such as, for example, in conventional "first pass" angiography. For example, see copending patent application Ser. No. 07/409,249 assigned to the instant assignee and is incorporated by reference herein.

Other radiations can also be used in combination with the collimator assembly 10 such as, ions, neutrons, positrons, X-rays, electrons and the like. A desired gamma ray portion 30 of the gamma rays 26 travel along a substantially parallel line 32 or within a very narrow angular range within which the gamma ray portion 30 does not strike the collimator assembly 10. The desired gamma ray portion 30 thus passes undisturbed through the collimator assembly 10. This desired gamma ray portion 30 is sensed by a conventional detector 34, such as, a gamma ray counter of a conventional Anger camera or a sensor of a first pass cardiac inspection system, such as the angiographic system of Scinticor Incorporated of Milwaukee, Wis.

In addition to the desired gamma ray portion 32, having a substantially unchanged primary energy $E_0$ after emission from the radiation source, there is a substantial fraction of divergent gamma rays 31 from the specimen 28. These divergent gamma rays 31 interact with the collimator walls 18 and result in diminished resolution of spatial features of the specimen 28. The desirability of removing such divergent gamma rays 31 is well known. For example, in U.S. Pat. No. 4,096,389 (which is incorporated by reference herein) the benefits of effective collimation, generally, are described for X-ray and gamma ray radiographic imaging technology. Such advantages also are apparent for other conventional radiographic systems, such as in emission tomography systems and Anger camera geometries (see, for example, U.S. Pat. Nos. 4,295,047; 4,682,033; 4,852,142; 4,672,648; and 4,277,684, which are incorporated by reference herein).

The divergent gamma rays 31 interact with the collimator walls 18 and the divergent gamma rays 31 lose energy, creating inelastic scattered radiation 36 having energies less than $E_0$ of the initial gamma rays 26. In order to achieve optimum resolution, the divergent gamma rays 31 (and the inelastic scattered byproduct radiation) should be substantially removed by the collimator assembly 10. Removal of the inelastic scattered radiation 36 would allow sensing and analysis of only the desired gamma ray portion 30 which is substantially parallel to line 32 in FIG. 2 and includes undisturbed gamma rays 30 from the specimen 28. This desired gamma ray Portion 30 is then sensed by detector 34. This enables achieving the desired level of resolution for the features of the specimen 28.

As mentioned hereinbefore, the divergent gamma rays 31 before interaction with the collimator walls 18 have an energy of $E_0$, and after wall interaction the inelastic scattered radiation 36 includes a range of electromagnetic wave energies, from $E_0$ at a maximum to lesser values. In the case of an inelastic interaction, the divergent gamma rays 31 interact with the lead structure 20 of the collimator assembly 10. When the gamma rays 31 (such as, cobalt radionuclide gamma rays having an energy of roughly 140 KeV) enter the lead structure 20, energy can be lost by a variety of processes. For example, energy can be lost by excitation of electrons from the ground state in each of the lead atoms. These excited electrons return to their ground state energy level and simultaneously emit a characteristic X-ray, such as Pb K-alpha radiation having an energy of about 74 KeV. Numerous other electron excitations and decays to ground state occur, giving rise to lower energy X-rays and other electromagnetic wave species which are preferentially absorbed within the lead structure 20. These events normally occur without reemitting any X-rays into the collimator free space outside the lead structure 20, and thus the lower energy radiation is not normally detected by the detector 34.

Therefore, as stated above, when the divergent gamma rays 31 enter the lead structure 20, a 74 KeV X-ray can escape into free space as a consequence of inelastic scattering of the 140 KeV cobalt gamma ray. This emitted 74 KeV inelastic scattered X-ray 36 travels along line 42 (see FIG. 2) and is sensed by the detector 34. Conventional energy discriminators in an electronic detection system 37 (shown schematically), which is coupled to the detector 34, can remove the unwanted signal arising from the inelastic scattered X-ray 36. However, such a sensed event can cause substantial loss of resolution which is detrimental to spatial (or angular) resolution. This loss of resolution can result because the event is still counted by the counter 34 and prevents detection of the desired undeviated gamma ray portion 32. Conventional counter electronics in the detection system 37 can only count at a given finite rate, such as, for example, 100,000 to 1,000,000 counts per second, and detection of unwanted energetic photons (or particles) prevents accumulating a desired event. The need to maximize useful signal (coupled with the limits on the ability of the electronics to count all incoming events) makes it imperative to remove the emitted, or inelastically scattered, X-rays 36 in order to use the full capacity of the counter 34 to sense the desired gamma ray portion 30.

In FIGS. 2 and 3 is shown the layered wall structure of the collimator assembly 10. This layered wall structure enables detection of substantially only the gamma rays 30 and by removal of the unwanted inelastic scattered X-rays 36 so such a component is not sensed by the detector 34. As shown in the preferred embodiment, the thin layer 22 is tin but can be any material which exhibits a large absorption coefficient for the energetic inelastic scattered X-rays 36 emitted from the underlying lead structure 20. The tin layer 22 can be quite thin (for example, about ¼ mm) and still be quite effective in absorbing the inelastic scattered lead K-alpha X-rays 36. As can be understood from conventional X-ray optics (and other appropriate spectroscopic sciences, such as ion optics) the only portion of energetic photons which might be sensed by the detector 34 is emitted primarily at relatively small angles with respect to the line 32. The geometry of the collimator assembly 10, including the length "l" in FIG. 2 and the other dimensions (see FIG. 3) result in the reemitted inelastic scatterd X-rays 36 traveling over a substantial path length within the tin layer 22. As a consequence of the large path length travelled at such small angles relative to direction 32, and the well known exponential absorption attenuation, the tin layer 22 is very effective in removing the unwanted inelastic scattered X-rays 36. The ratio of transmitted intensity to initial intensity is exp $(-\mu \cdot t)$, where $\mu$ is the well known linear absorption coefficient of tin (about 28.1 cm$^{-1}$ at 75 Kev), and "t" is the path length travelled by the inelastic scattered X-rays 36 in the tin layer.

Figure 5A:
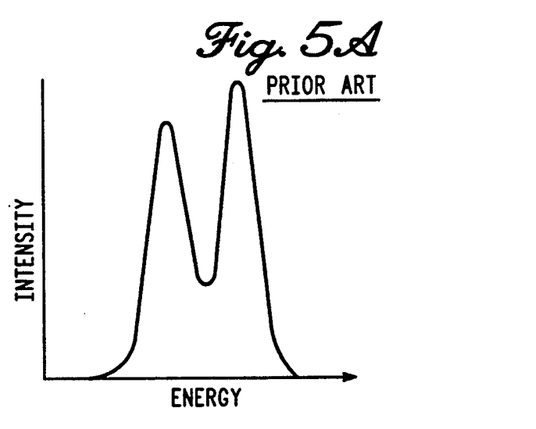
FIG. 5A illustrates the detected radiation spectra from a cobalt radionuclide source using a conventional lead collimator assembly and FIG. 5B shows the radiation spectra using the layered lead-tin collimator assembly of the invention.
Figure 5B:
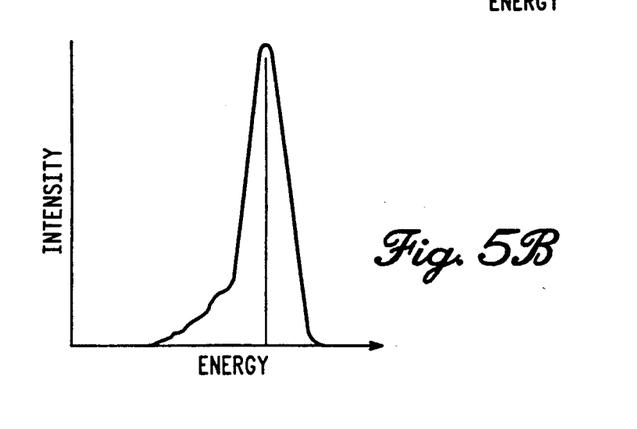

The effect of the collimator assembly 10 on reducing the X-rays 36 is demonstrated dramatically by comparing FIGS. 5A and 5B. FIG. 5A shows the radiation sensed by the detector 34 in a Scinticor angiographic system for a collimator system having only a lead base structure. As can be seen in FIG. 5A, there are two prominent peaks sensed, one peak at about 75 KeV associated with the lead K-alpha inelastically scattered X-rays 36 and the second cobalt gamma ray peak at about 140 KeV. The nearly equal prominence of the intensity of the two peaks points out the significance of removing the inelastic scattered X-rays 36. In FIG. 5B is shown the energy spectrum detected employing the collimator assembly 10 with substantially identical collimator dimensions.

Figure 6:
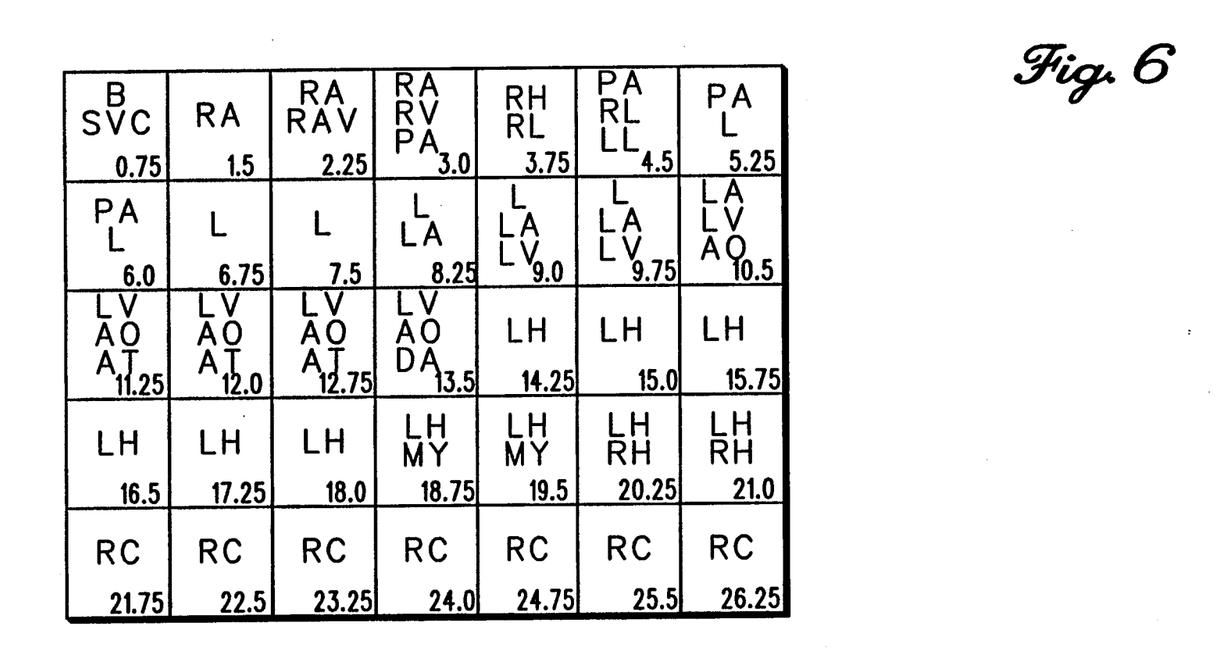
FIG. 6 shows a chart of the explanation key for each block of a matrix of a time lapse photographs of a patient's cardiac system.

As demonstrated by the data of FIG. 5, the collimator assembly 10 is highly effective in the removal of the lead K-alpha inelastic scatterred X-rays 36, thus enabling the detector 34 to sense only the desired gamma ray portion 30. Consequently, the efficiency of detection for a given radionuclide source intensity in the specimen 28 can be substantially enhanced. As determined by actual experiment in Scinticor angiographic systems this is about 50 percent for the illustrated embodiment wherein the number of 140 KeV events detected increases, for example, from about 400,000 to 600,000 counts Per second. Such an improvement in efficiency also results in enhanced signal which manifests itself as improved image resolution of the specimen cardiac system. For example, as shown by the angiographic image data of FIGS. (6i–6viii), a cardiologist is now able to resolve critical features previously unresolvable. The use of the collimator assembly 10 has, however, substantially improved resolution such that high quality first pass angiography can now be performed routinely.

For example, as shown by the angiographic image data of FIGS. 6-14, a cardiologist is now able to resolve critical features previously unresolvable. The use of the collimator assembly 10 has, therefore, substantially improved resolution such that high quality first pass angiography can now be performed routinely. A shown in FIGS. 7-14, the resulting images are of high quality, enabling a cardiologist to more effectively perform diagnoses previously made without the benefit of such detailed medical information.

Figure 7:
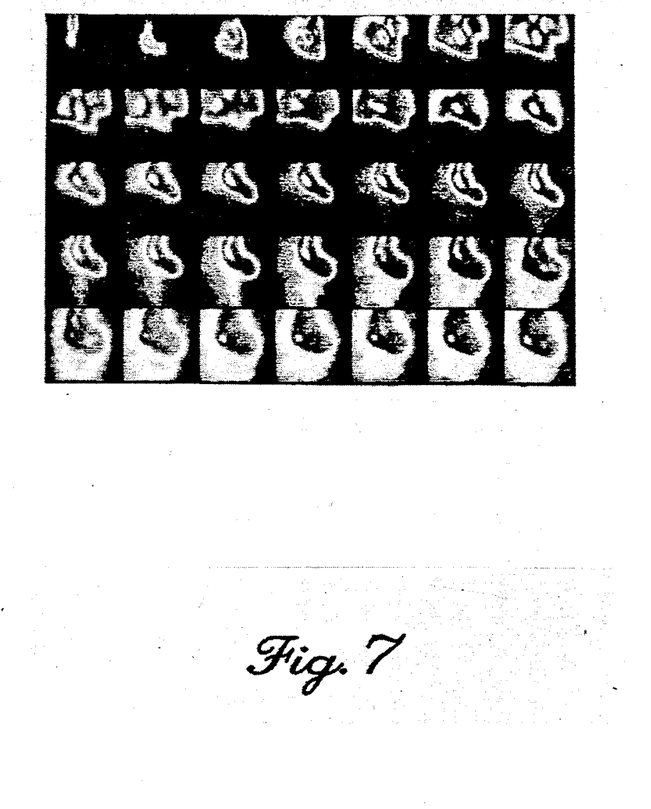
FIG. 7 shows an example time lapse photograph for a matrix of photographs of a patient's cardiac system in a radionuclide angiographic (RNA) study.

In regard to the angiographic image data, FIG. 7 shows an example time lapse photograph for each block of a matrix of time lapse photographs of a patient's cardiac system in an RNA (radionuclide angiographic) study on a SIM400. This figure illustrates passage of a bolus through the central circulation during a first pass RNA study. FIG. 6 shows the explanation key for the matrix of time lapse photographs of FIGS. 7-14, and the numbers in the lower right hand corner of FIG. 6 are elapsed time in seconds. These images are compressed by a factor of thirty times the original framing rate.

Figure 8A:
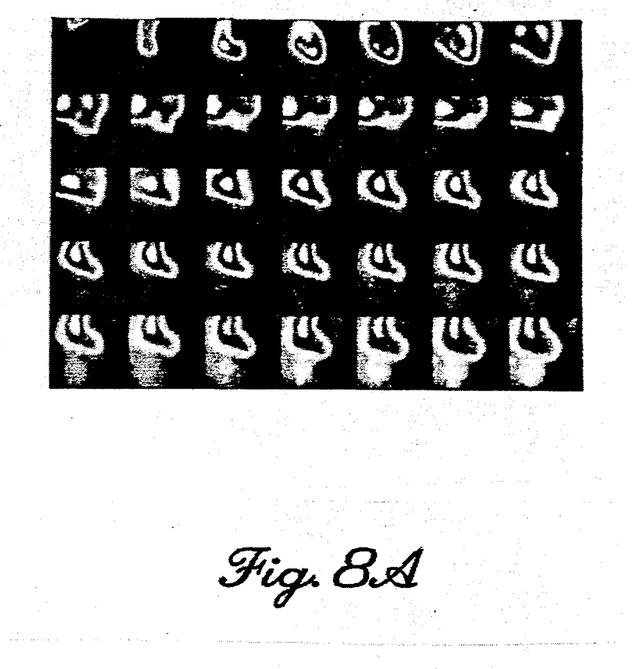
FIG. 8A shows an RNA study for a patient Beau using a conventional lead collimator and FIG. 8B shows an RNA study for patient Beau using a tin/lead collimator form of the invention.
Figure 8B:
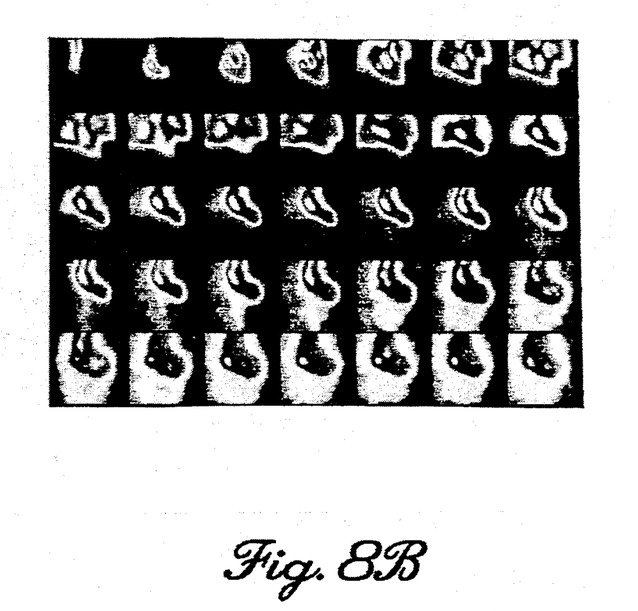

The abbreviation keys in FIG. 6 are referenced as follows:

Image Descriptions (Read from left to right and top to bottom.)
Key
B-Bolus
RA-Right Atrium
PA-Pulmonary Artery
LL-Left Lung
L-Lungs; includes RL and LL
LA-Left Atrium
LV-Left Ventricle
AO-Proximal Aorta
AT-Aortic Outflow Track
DA-Descending Aorta
MY-Myocardium
LH-Left Heart; includes LA, LV, AO, AT, DA
RC-Recirculation; includes LH and RH
SVC-Superior Vena Cava
RV-Right Ventricle
RH-Right Heart includes RA, RV, PA
RL-Right Lung FIG. 8A is an RNA study performed Sep. 22, 1989 on patient Beau using the Conventional Lead Collimator on SIM400. FIG. 8B is another RNA study performed on patient Beau. The study was performed Sep. 18, 1990 using a research model of the Tin/Lead Collimator on SIM400. The conclusions reached are that RH, L, and LH phases are clearly better imaged with the Tin/Lead Collimator in FIG. 8B than FIG. 8A and that the LV is especially better defined in FIG. 8B. Note that the study parameters were essentially identical in both FIGS. 8A and 8B studies; these include bolus technique, dose, patient positioning, image processing, and all hardware except the collimators.

Figure 9A:
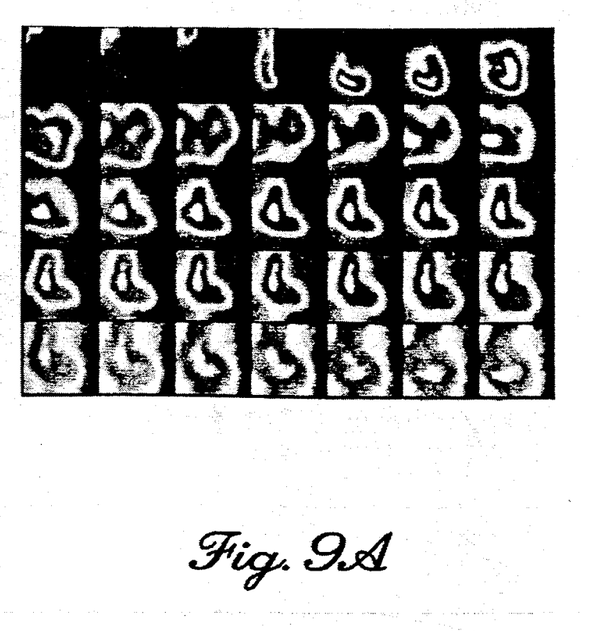
FIG. 9A shows an RNA study for a patient Cul using a conventional lead collimator and FIG. 9B shows an RNA study for patient Cul using a tin/lead collimator form of the invention.
Figure 9B:
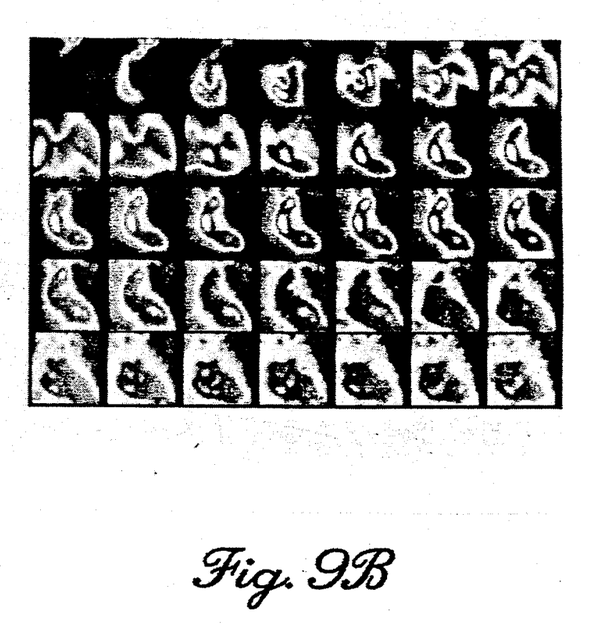

In FIG. 9A is shown data for patient Cul. An RNA study was performed on Jun. 9, 1989 using the Conventional Lead Collimator on SIM400. Another RNA study was performed on patient Cul on Sep. 5, 1990 using a research model of the Tin/Lead Collimator on SIM400 as illustrated in FIG. 9B. The study concluded (a) that the RH and LH chambers are more clearly delineated in FIG. 9B; (b) the LV, RV and PA are better resolved in FIG. 9B than 9A; and (c) the valve planes are not delineated in FIG 9A, especially the pulmonary valve between RV and PA and the Aortic valve between LV and 40 which are clearly visualized in FIG 9B. Note the study parameters and protocols are essentially identical in FIGS. 9A and 9B except for the collimators as indicated.

Figure 10A:
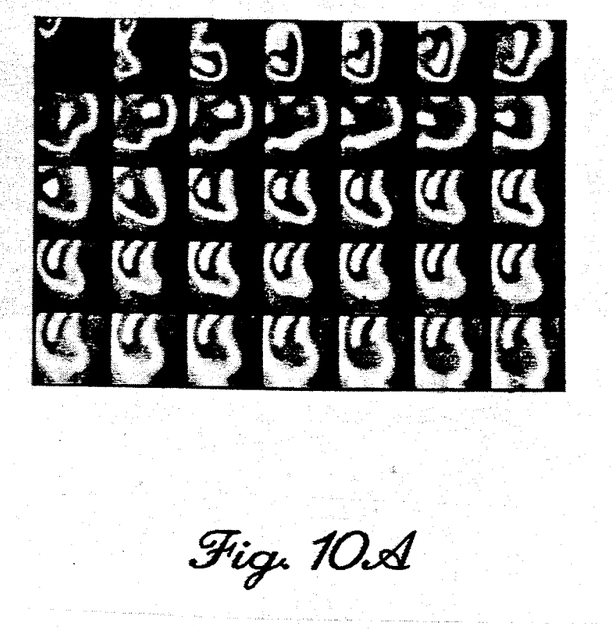
FIG. 10A shows an RNA study for a patient Rose using a conventional lead collimator and FIG. 10B shows an RNA study for patient Rose using a tin/lead collimator form of the invention.
Figure 10B:
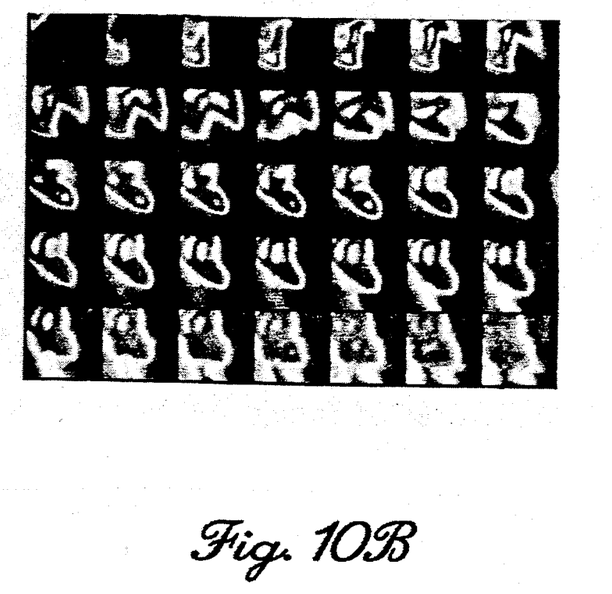

FIG. 10A illustrates the results of an RNA study performed on patient Rose on May 5, 1989 using the Conventional Lead Collimator on SIM400. Another RNA study was performed on patient Rose on Sep. 10, 1990 using a research model of the Tin/Lead Collimator on SIM400. The study concluded that (a) the LV in FIG. 10B is well visualized from the Aortic valve plane to the apex compared to FIG. 10A which merges the LV with the AO; (b) the LL in FIG. 10 is well separated from the LV chamber strongly suggesting that FIG. 10B has much reduced anatomic background and Compton scatter background compared to FIG. 10A; and (c) the AO valve plane is clearly visualized in FIG. 10B but burnt out by saturated counts in the AT in FIG. 10A. Note the study parameters and protocols were essentially identical in both RNA studies except for the collimators as indicated.

Figure 11A:
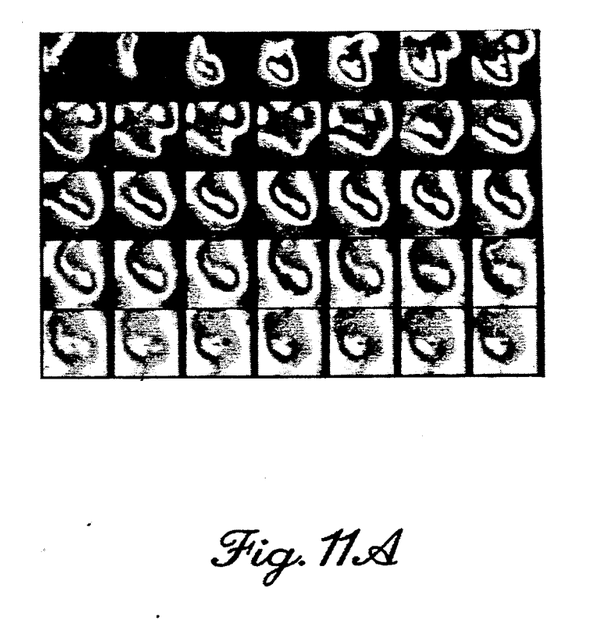
FIG. 11A shows an RNA study for a patient Badu using a conventional lead collimator and FIG. 11B shows an RNA study for patient Badu using a tin/lead collimator form of the invention.
Figure 11B:
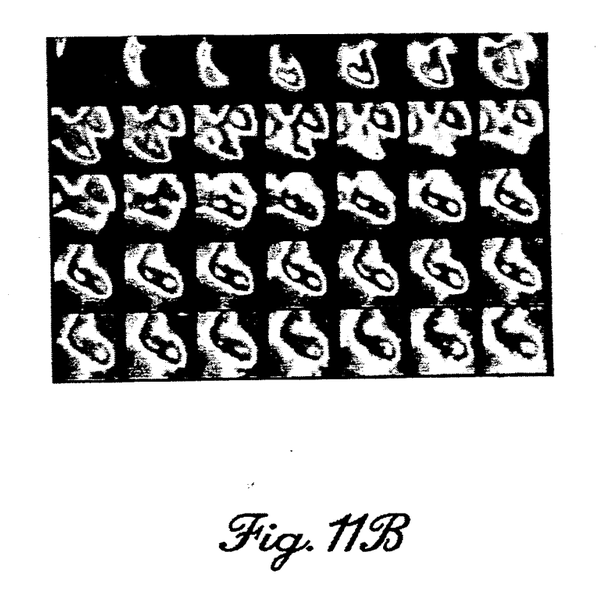

The Conventional Lead Collimator was used in an RNA study performed Jun. 21, 1989 on patient Badu illustrated in FIG. 11A. In FIG. 11B is shown data for another study on patient Badu. This figure illustrates the (—NORTH—)y study performed Aug. 22, 1990 using a research model of the Tin/Lead Collimator on SIM400. The conclusions of the study are as follows: (a) FIG. 11B clearly shows improved resolution and contrast compared to FIG. 11A; (b) the LV is better resolved in FIG. 11B; and (c) the lungs are well separated from the Right and Left Ventricular chambers in FIG. 11B compared to FIG. 11A. This leads to a 50% reduction in lung background over the LV in FIG. 11B compared to FIG. 11A. The study parameters and protocols were essentially identical in both studies of FIGS. 11A and 11B except for the collimators as indicated.

Figure 12A:
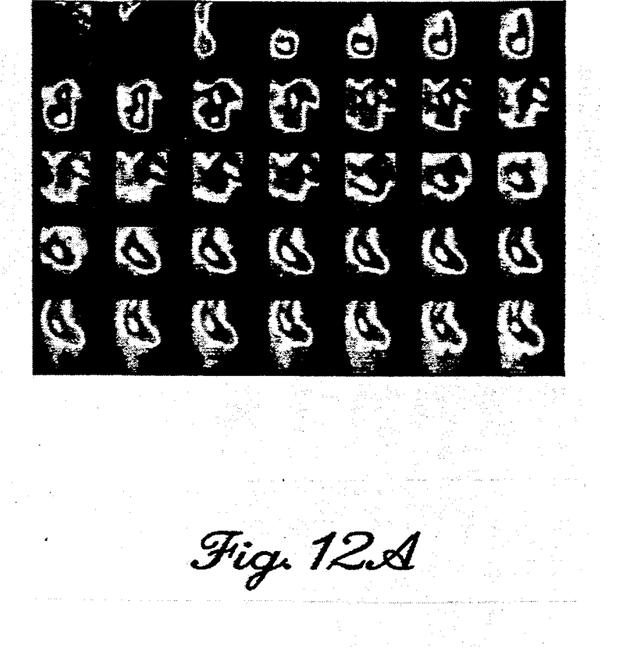
FIG. 12A shows an RNA study for a patient Quag using a conventional lead collimator and FIG. 12B shows an RNA study for patient Quag using a tin/lead collimator form of the invention.
Figure 12B:
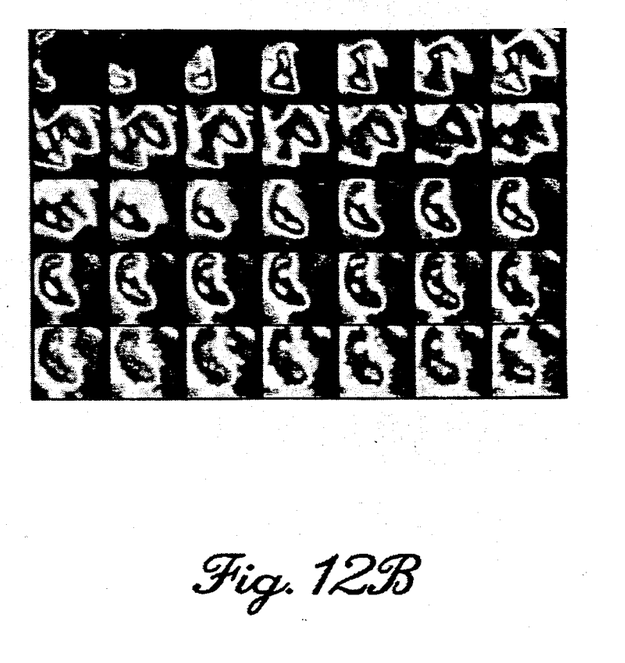

An RNA study was performed on patient Quag on Jun. 26, 1989 using the Conventional Lead Collimator on a conventional System 77 as is illustrated in FIG. 12A. FIG. 12B shows another RNA study of patient Quag performed Aug. 17, 1990 using a research model of the Tin/Lead Collimator on SIM400. The study concluded that the RV, LV and valve planes between RV and PA and between LV and AO are all better visualized in FIG 12B compared to FIG. 12A and that the DA and onset of myocardial blush can be seen in FIG. 12B but not in FIG. 12A. This is an important comparison because FIG. 12A was performed on System 77 which has been the gold standard of RNA studies since 1972 and, until the research on SIM400 with the development of the Tin/Lead collimator, the System 77 represented the state of the art in First Pass collimators. The study parameters and protocols were essentially identical in both studies (FIGS. 12A and 12B). Both received the same image processing treatment on a SIM400.

Figure 13A:
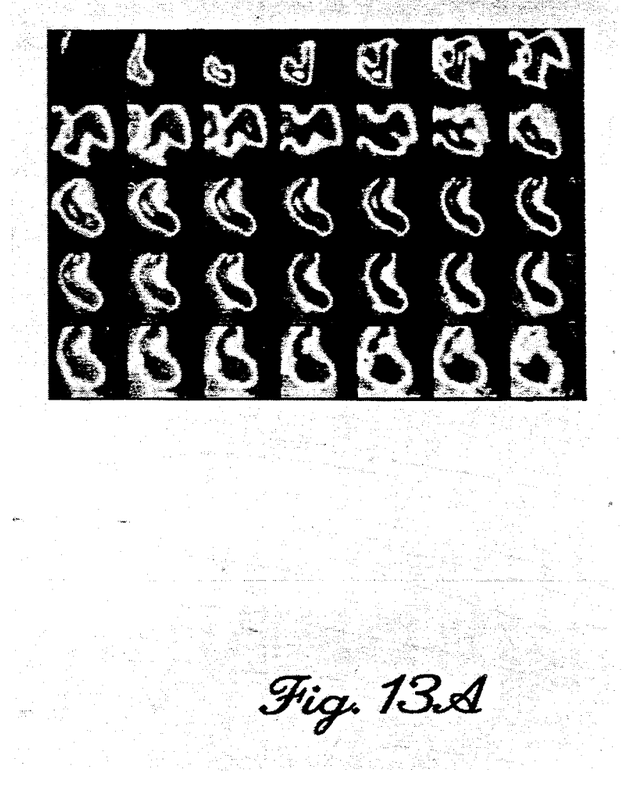
FIG. 13A shows an RNA study for a patient Chak using a high resolution lead collimator.
Figure 13B:
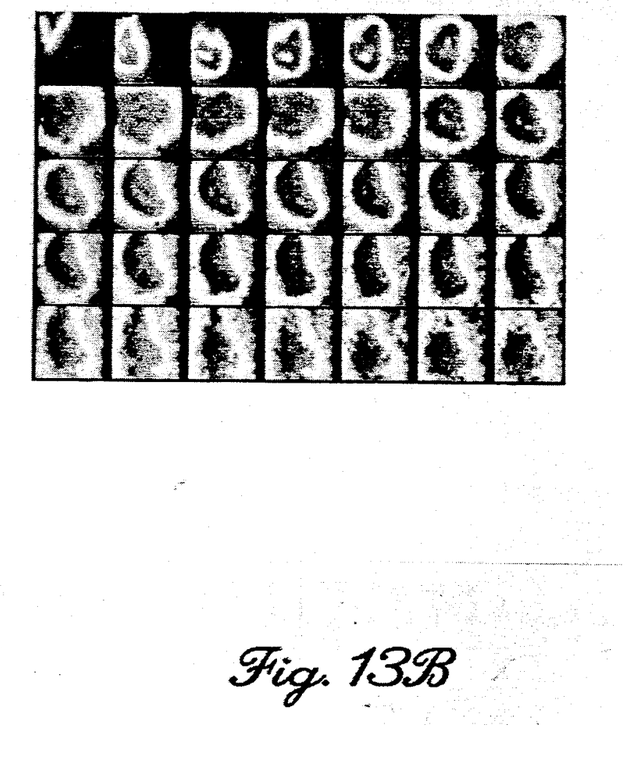
FIG. 13B shows a study for the patient performed using a simultaneous dual energy method; and 13C shows an RNA study for the patient Chak using a tin/lead collimator form of the invention.
Figure 13C:
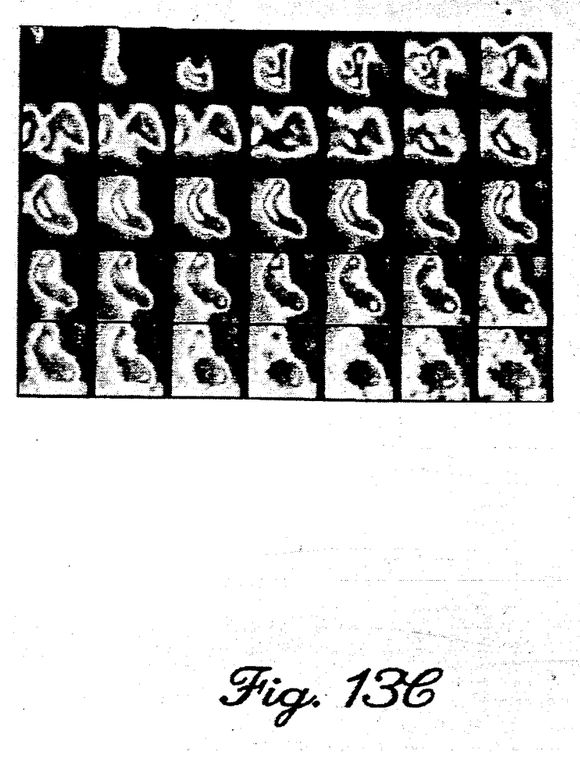

FIG. 13A shows data from a study performed on patient Chak in which a high spatial resolution dead collimator was used. Such collimators are not normally used in first pass studies because of its low efficiency. However, this study shows that spatial resolution alone cannot bring a first pass study to the quality achieved with the Tin/Lead collimator of FIG. 13C. The reason for this is shown in the Compton Scatter Image obtained in FIG. 13B. The data of FIG. 13B were obtained by performing a simultaneous dual energy study to allow a comparison of imaging a first pass RNA study with photopeak events and Compton Scatter and Pb X-ray events. This panel clearly shows the poor image quality that results from scatter and Pb X-ray events. The purpose of the Tin/Lead collimator is to reduce this imaging component. In FIG. 13C is shown an image produced in an RNA study performed on patient Chak on Aug. 17, 1990 using a Tin/Lead collimator. This study is superior to the photopeak study of FIG. 13A even when it is performed with the most highly optimized conventional lead collimator and high spatial resolution. It can be seen that the pure scatter/Pb X-ray image illustrated in this figure bears a tell-tale resemblance to the images shown using the conventional lead collimator.

Figure 14A:
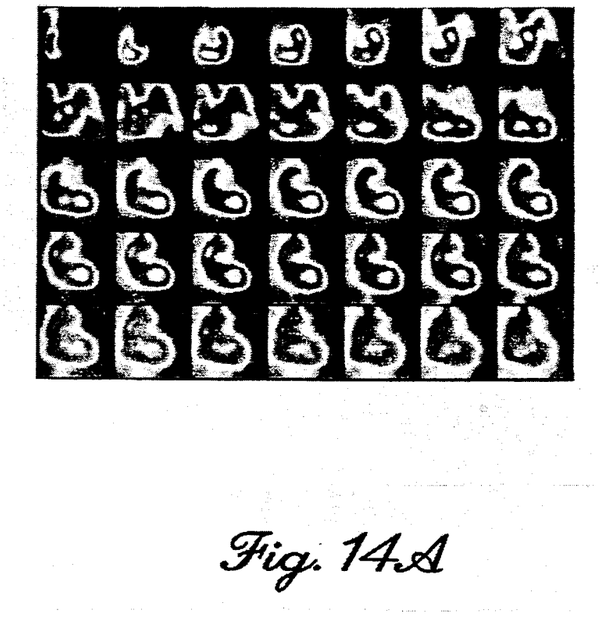
FIG. 14A shows an RNA study for a patient Mel using a conventional lead collimator and FIG. 14B shows an RNA study performed using a slow bolus mode with a tin/lead collimator form of the invention.
Figure 14B:
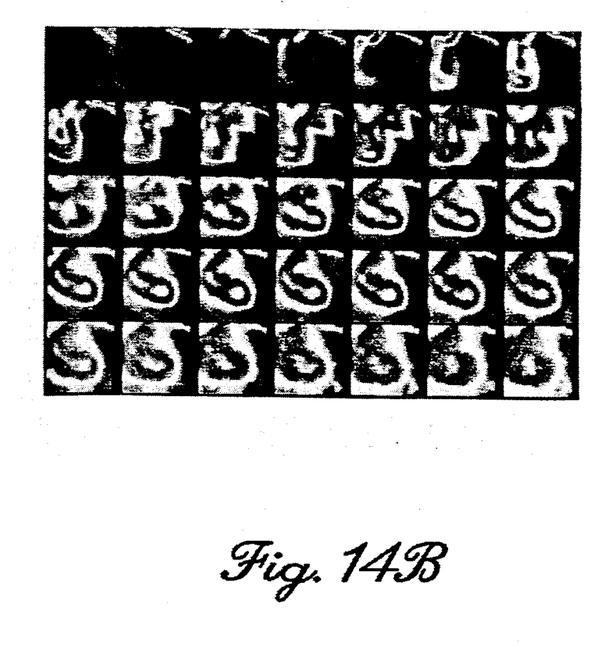

FIG. 14A is an image resulting from an RNA study performed on patient Mel on Jul. 31, 1989 using the conventional lead collimator on SIM400. FIG. 14B shows an image which was produced in a slow bolus study also performed on patient Mel on Sep. 4, 1990 using a research model of the Tin/Lead collimator on SIM400. The study concluded that FIGS. 14A and 14B are somewhat comparable in quality.

Preferably, the tin layer 22 does not have too high an atomic number, or the thin layer 22 can itself reemit a high energy X-ray which could be transmitted through the thin layer 22 and be sensed by the detector 34. Knowing the composition of the base structure 20, one can apply conventional radiation absorption knowledge and methods to determine the appropriate materials and their layer thicknesses necessary to absorb a substantial fraction of any inelastic scattered radiation, particularly emitted K alpha and L alpha X-rays from the base collimator structure 20. This basic concept of layered wall collimators can be applied to any radiation collimator, such as for X-rays, ions, infrared laser light, positrons, electrons, neutrons and microwave or other photon energies. Associated with each of these radiations is a known, developed knowledge of absorption and inelastic scattering events. In those instances in which inelastic scattered radiation can be produced, such unwanted data can be preferentially removed in the manner described.

The efficiency of the gamma ray collimator assembly 10 can be assessed with reasonable accuracy for the square cross section collimator geometry illustrated in FIG. 3. The efficiency is expressed in terms of the spatial dimensions:

$E = A_1 A_2 / 4\pi l^2 M^2$ $A_1$ = area of lead square (edge "b" squared)

$A_2$ = area of tin square (edge "a" squared)

l = longitudinal length of collimator passageway (see FIG. 2)

M = center to center spacing (see FIG. 2)

Thus, one can select a desired efficiency by adjusting the various geometries of the collimator assembly 10.

In another aspect of the invention the collimator assembly 10 can be constructed of any desired height and longitudinal length l, along the collimator assembly 10. The user can then assemble a final collimator assembly 10 of any desired length of longitudinal passageway by stacking two or more different height collimator assemblies.

While preferred embodiments of the invention have been shown and described, it will be clear to those skilled in the art that various changes and modifications can be made without departing from the invention in its broader aspects as set forth in the claims provided hereinafter.

I claim:

1. A collimator assembly for removing selected radiation output from a specimen under inspection, comprising a plurality of collimator elements wherein each of said collimator elements comprises walls defining an elongated longitudinal passageway, said walls absorbing divergent portions of said selected radiation from said specimen and said walls comprised of a first material covered by an inner layer of a second material adjacent the longitudinal passageway, said second material effectively removing said selected radiation which has been inelastically scattered from said first material with said inelastically scattered form of said selected radiation thereby having less energy than said selected radiation.

2. The collimator assembly as defined in claim 1 wherein said selected radiation comprises gamma rays.

3. The collimator assembly as defined in claim 1 wherein said selected radiation comprises X-rays.

4. The collimator assembly as defined in claim 1 wherein said selected radiation comprises positrons.

5. The collimator assembly as defined in claim 1 wherein said selected radiation comprises fast neutrons.

6. A method of collimating ionizing electromagnetic gamma radiation, comprising the steps of:
   selecting a particular gamma radiation for collimation, said radiation output from a specimen of interest;
   positioning a detector of said particular radiation in a location useful for gathering information about said specimen and associated with said particular radiation; and
   using a collimator with each collimator element having a longitudinal passageway and a layered wall structure wherein divergent portions of said particular radiation interact with said layered wall structure, giving rise to inelastically scattered radiation of the same general type as said particular radiation but with less energy and said inelastically scattered radiation is effectively removed by said layered wall structure.

7. The method as defined in claim 6 wherein said collimator comprises a first thin layer material disposed nearest the non divergent portion of said particular radiation passing through said longitudinal passageway with said first layer material having a high preferential absorption for said inelastic scattered spectra.

8. The method as defined in claim 6 wherein said layered wall structure comprises a thin tin layer on a base structure of lead.

9. A method of constructing a gamma ray collimator, comprising the steps of:
   assembling a plurality of base lead collimator elements; and
   disposing a thin layer of tin on said lead collimator elements, said layer of tin being thick enough to effectively remove inelastic scattered high energy photons arising from gamma rays striking said base lead collimator elements.

10. The method as defined in claim 9 further including the steps of stacking layers of said assembled collimator elements to form a desired length of longitudinal passageway for said collimator elements to collimate said gamma rays.

11. The method as defined in claim 10 wherein selected ones of said stacked layers further include an inserted egg crating matrix with each longitudinally extending wall of said matrix comprised of a lead center portion with a thin inner tin layer disposed thereon.

12. The method as defined in claim 9 further including the step of inserting an egg crating matrix into said plurality of collimator elements to provide additional resolution.

13. The method, as defined in claim 12 wherein each said collimator element comprises a square lead tubing element and a square tin tubing element.

* * * * *